(12) United States Patent
Suyama (10) Patent No.: US 11,389,344 B2
(45) Date of Patent: Jul. 19, 2022

(54) ABSORBENT PAD

(71) Applicant: DAIO PAPER CORPORATION, Ehime (JP)

(72) Inventor: Junnosuke Suyama, Tochigi (JP)

(73) Assignee: DAIO PAPER CORPORATION, Ehime (JP)

(*) Notice: Subject to any disclaimer, the term of this patent is extended or adjusted under 35 U.S.C. 154(b) by 485 days.

(21) Appl. No.: 16/493,005

(22) PCT Filed: Mar. 6, 2018

(86) PCT No.: PCT/JP2018/008472
§ 371 (c)(1),
(2) Date: Sep. 11, 2019

(87) PCT Pub. No.: WO2018/173735
PCT Pub. Date: Sep. 27, 2018

(65) Prior Publication Data
US 2020/0060896 A1 Feb. 27, 2020

(30) Foreign Application Priority Data

Mar. 21, 2017 (JP) .............................. JP2017-055037

(51) Int. Cl.
*A61F 13/53* (2006.01)
*A61F 13/535* (2006.01)
(Continued)

(52) U.S. Cl.
CPC .......... *A61F 13/535* (2013.01); *A61F 13/513* (2013.01); *A61F 13/514* (2013.01);
(Continued)

(58) Field of Classification Search
CPC ........ A61F 13/525; A61F 2013/530481; A61F 2013/53051; A61F 2013/530547;
(Continued)

(56) References Cited

U.S. PATENT DOCUMENTS 4,994,053 A * 2/1991 Lang .................... A61F 13/5323
428/323
9,532,909 B2 * 1/2017 Umebayashi ......... B29C 66/433
(Continued)

FOREIGN PATENT DOCUMENTS

CN 103096852 A 5/2013
EP 2 441 418 A1 4/2012
(Continued)

OTHER PUBLICATIONS

Extended European Search Report dated Feb. 10, 2020, in connection with corresponding EP Application No. 18770899.5; 6 pages.
(Continued)

*Primary Examiner* — Catharine L Anderson
(74) *Attorney, Agent, or Firm* — Maier & Maier, PLLC (57) ABSTRACT

Disclosed is an absorbent pad which efficiently diffuses excretory fluid and gives no sense of discomfort to a wearer even after excretion. A front sheet and a rear sheet are joined to each other at a plurality of first junctions and a plurality of second junctions, and when viewed in plan, the first junctions extending in a longitudinal direction are arranged at predetermined intervals in a width direction, and second junctions extending in the width direction are arranged at predetermined intervals in the longitudinal direction. A plurality of cells, each of which is defined by an adjacent pair of the first junctions and an adjacent pair of the second junctions, is formed between the front sheet and the rear sheet spaced apart from each other. An opening extending in the longitudinal direction is formed in at least one of the first junctions.

6 Claims, 10 Drawing Sheets

(51) Int. Cl.
  *A61F 13/513* (2006.01)
  *A61F 13/514* (2006.01)
  *A61F 13/515* (2006.01)

(52) U.S. Cl.
  CPC .. *A61F 13/515* (2013.01); *A61F 2013/53051* (2013.01); *A61F 2013/530992* (2013.01)

(58) Field of Classification Search
  CPC ........ A61F 2013/530554; A61F 2013/530562; A61F 2013/530875; A61F 2013/530992
  See application file for complete search history.

(56) References Cited

U.S. PATENT DOCUMENTS

| | | | |
|---|---|---|---|
| 9,693,911 B2 * | 7/2017 | Sheldon | A61F 13/5376 |
| 11,020,291 B2 * | 6/2021 | Konawa | A61F 13/51104 |

FOREIGN PATENT DOCUMENTS

| | | |
|---|---|---|
| JP | S59159420 U | 10/1984 |
| JP | 2009-131510 A | 6/2009 |
| JP | 2015-112401 A | 6/2015 |
| JP | 2016-43193 A | 4/2016 |
| WO | 2011/070728 A1 | 6/2011 |

OTHER PUBLICATIONS

Chinese Office Action dated Mar. 1, 2021, in connection with corresponding CN Application No. 201880019140.X (10 pp., including machine-geenrated English translation).

Japanese Office Action dated Jul. 10, 2018, in connection with corresponding JP Application No. 2017-055037 (10 pp., including machine-generated English translation).

Translation of International Search Report dated Jun. 5, 2018 and Written Opinion of corresponding application No. PCT/JP2018/008472; 10 pgs.

* cited by examiner

ABSORBENT PAD

FIELD

The present invention relates to an absorbent for use in absorbent articles such as disposable diapers, napkins, and pads, particularly to an absorbent pad made of an absorbent polymer.

BACKGROUND

A prior art proposes a technique of forming an absorbent pad for a disposable diaper including a liquid permeable front sheet, a liquid permeable rear sheet, and an absorbent polymer sandwiched between the front sheet and the rear sheet, and providing the absorbent pad with openings extending in the longitudinal direction and arranged at predetermined intervals in the width direction when viewed in plan (Patent Document 1).

Another prior art proposes a technique of forming an absorbent pad for a disposable diaper including a liquid permeable front sheet, a liquid permeable rear sheet, pulp fibers and an absorbent polymer sandwiched between the front sheet and the rear sheet, and providing the absorbent pad with cuts, on the front sheet, discontinuous in the width direction and arranged at predetermined intervals in the longitudinal direction when viewed in plan (Patent Document 2).

Patent Document 1: Japanese Unexamined Patent Publication No. 2015-112401

Patent Document 2: Japanese Unexamined Patent Publication No. 2016-43193

SUMMARY

According to the technique of Patent Document 1, excretory fluid that has reached the front sheet is not diffused over the entire area of the front sheet, and a portion of the excretory fluid not absorbed by the absorbent pad may possibly leak to the outside.

According to the technique of Patent Document 2, the pulp fibers and the absorbent polymer sandwiched between the front sheet and the rear sheet thicken the absorbent pad. This may cause a wearer to feel discomfort not only after excretion but also before excretion.

In view of the foregoing, it is therefore an object of the present invention to provide an absorbent pad which efficiently diffuses the excretory fluid and gives no sense of discomfort to a wearer even after excretion.

The object of the present invention has been achieved in the following manner. A first aspect of the present invention is directed to an absorbent pad including a liquid permeable front sheet, a liquid permeable or impermeable rear sheet, and absorbing polymer particles disposed between the front sheet and the rear sheet, the absorbent polymer particles absorbing excretory fluid. The front sheet and the rear sheet are joined to each other at a plurality of first junctions and a plurality of second junctions. When viewed in plan, the first junctions each extending in a longitudinal direction are arranged at predetermined intervals in a width direction, and the second junctions each extending in the width direction are arranged at predetermined intervals in the longitudinal direction. A plurality of cells, each of which is defined by an adjacent pair of the first junctions and an adjacent pair of the second junctions, is formed between the front sheet and the rear sheet spaced apart from each other. The absorbent polymer particles are provided in the cells. An opening extending in the longitudinal direction is formed in at least one of the first junctions.

A second aspect of the invention is an embodiment of the first aspect. In the second aspect, the cells includes first cells containing the absorbent polymer particles in a small amount and second cells containing the absorbent polymer particles in a large amount, and the first cells are arranged around both ends in the longitudinal direction of the opening.

A third aspect of the invention is an embodiment of the first or second aspect. In the third aspect, the opening includes a first opening provided at one of the first junctions at a center of the absorbent pad in the width direction, a second opening provided at one of the first junctions in a left portion of the absorbent pad in the width direction, and a third opening provided at one of the first junctions in a right portion of the absorbent pad in the width direction.

A fourth aspect of the invention is an embodiment of the third aspect. In the fourth aspect, a dimension of the first opening in the longitudinal direction is greater than dimensions of the second and third openings in the longitudinal direction.

A fifth aspect is an embodiment of the third or fourth aspect. In the fifth aspect, each of the first, second, and third openings is formed of discontinuous breaking openings.

A sixth aspect of the invention is an embodiment of the fifth aspect. In the sixth aspect, when viewed in plan, the second opening is formed in an arc shape toward the center in the width direction, and the third opening is formed in an arc shape toward the center in the width direction.

According to the first aspect, the front sheet and the rear sheet are joined to each other at the plurality of first junctions and the plurality of second junctions. When viewed in plan, the first junctions each extending in a longitudinal direction are arranged at predetermined intervals in a width direction, and the second junctions each extending in the width direction are arranged at predetermined intervals in the longitudinal direction, a plurality of cells, each of which is defined by an adjacent pair of the first junctions and an adjacent pair of the second junctions, is formed between the front sheet and the rear sheet spaced apart from each other, the absorbent polymer particles are provided in the cells, and an opening extending in the longitudinal direction is formed in at least one of the first junctions. This allows the excretory fluid that has reached the front sheet to be quickly diffused on the entire area of the front sheet. Further, this can avoid concentration of the absorbent polymer particles, and can maintain high absorption performance of the absorbent pad. Thus, even when the absorbent pad becomes more rigid through absorption of the excretory liquid, a portion of the absorbent pad on the left of the opening and a portion of the absorbent pad on the right of the opening easily move back and forth in response to the walk of the wearer, thereby reducing the sense of discomfort given to the wearer.

According to the second aspect, in addition to the advantages achieved by the first aspect, the cells includes first cells containing the absorbent polymer particles in a small amount and the second cells containing the absorbent polymer particles in a large amount, and the first cells are arranged around the both ends in the longitudinal direction of the opening. This enables easy deformation of portions of the absorbent pad around both ends in the longitudinal direction of the opening in response to the walk of the wearer, and can reduce the sense of discomfort given to the wearer.

According to the third aspect, in addition to the advantages of the first or second aspect, the opening includes a first opening provided at one of the first junctions at a center of the absorbent pad in the width direction, a second opening provided at one of the first junctions in a left portion of the absorbent pad in the width direction, and a third opening provided at one of the first junctions in a right portion of the absorbent pad in the width direction. Hence, longitudinal movement of a portion of the absorbent pad on the left of the second opening can be made greater than longitudinal movement of a portion of the absorbent pad between the second opening and the first opening, and longitudinal movement of a portion of the absorbent pad on the right of the third opening can be made greater than longitudinal movement of a portion of the absorbent pad between the third opening and the first opening. This can block the dimensions of the first, second, and third openings in the width direction from exceeding a predetermined dimension.

According to the fourth aspect, in addition to the advantages of the third aspect, a dimension of the first opening in the longitudinal direction is greater than dimensions of the second and third openings in the longitudinal direction. This enables easy deformation of a portion of the absorbent pad on the left of the first opening and a portion of the absorbent pad on the right of the first opening in the longitudinal direction in response to the walk of the wearer, thereby further reducing the sense of discomfort given to the wearer.

According to the fifth aspect, in addition to the advantages of the third or fourth aspect, each of the first, second, and third openings is formed of discontinuous breaking openings. This can protect the cells arranged around the first opening, the second opening, and the third opening from break.

According to the sixth aspect, in addition to the advantages of the fifth aspect, when viewed in plan, the second opening is formed in an arc shape toward the center in the width direction, and the third opening is formed in an arc shape toward the center in the width direction. Hence, longitudinal movement of a portion of the absorbent pad on the left of the second opening can be made much greater than longitudinal movement of a portion of the absorbent pad between the second opening and the first opening, and longitudinal movement of a portion of the absorbent pad on the right of the third opening can be made much greater than longitudinal movement of a portion of the absorbent pad between the third opening and the first opening. This can further block the dimensions of the first, second, and third openings in the width direction from exceeding a predetermined dimension.

BRIEF DESCRIPTION OF THE DRAWINGS

FIG. 6A is cross-sectional views taken along line A-A in FIG. 5, where FIG. 6A illustrates a state before absorption of excretory fluid.

FIG. 6B is cross-sectional views taken along line A-A in FIG. 5, where FIG. 6B illustrates a state after absorption of excretory fluid.

DETAILED DESCRIPTION

<Disposable Diaper>

An absorbent pad of the present invention having high ability to diffuse liquid and causing less discomfort to a wearer using the absorbent pad will be described with reference to the accompanying drawings. In this specification, a "longitudinal direction" refers to a direction from a belly toward back of a wearer, a "width direction" refers to a direction orthogonal to the longitudinal direction, a "vertical direction" refers to a direction orthogonal to a waist direction of the disposable diaper in a worn state, an "inner surface" refers to a surface of each component facing a wearer's body, and an "outer surface" refers to a surface of each component opposite to the wearer's body.

Figure 1:
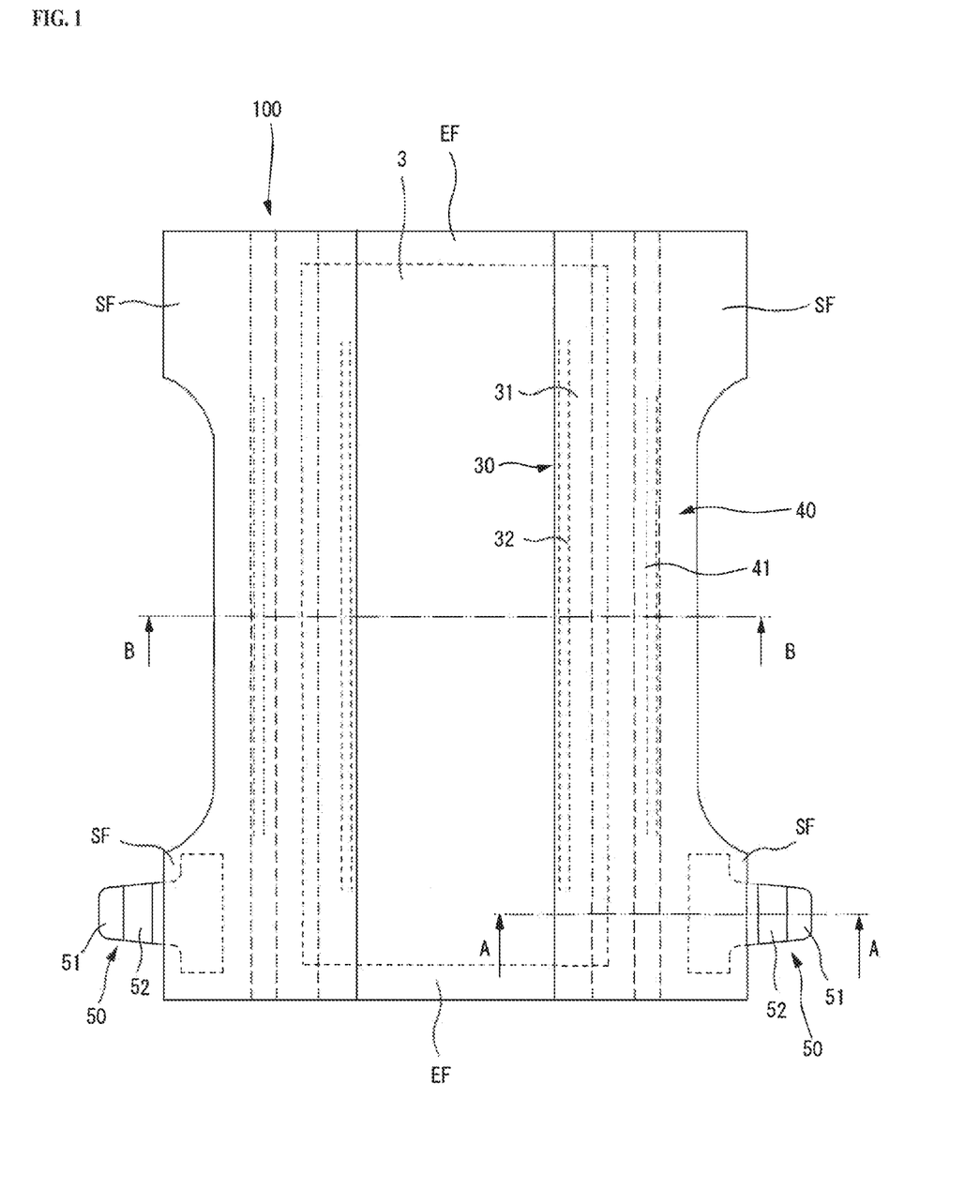
FIG. 1 is an interior plan view of a disposable diaper in a developed state.
Figure 2:
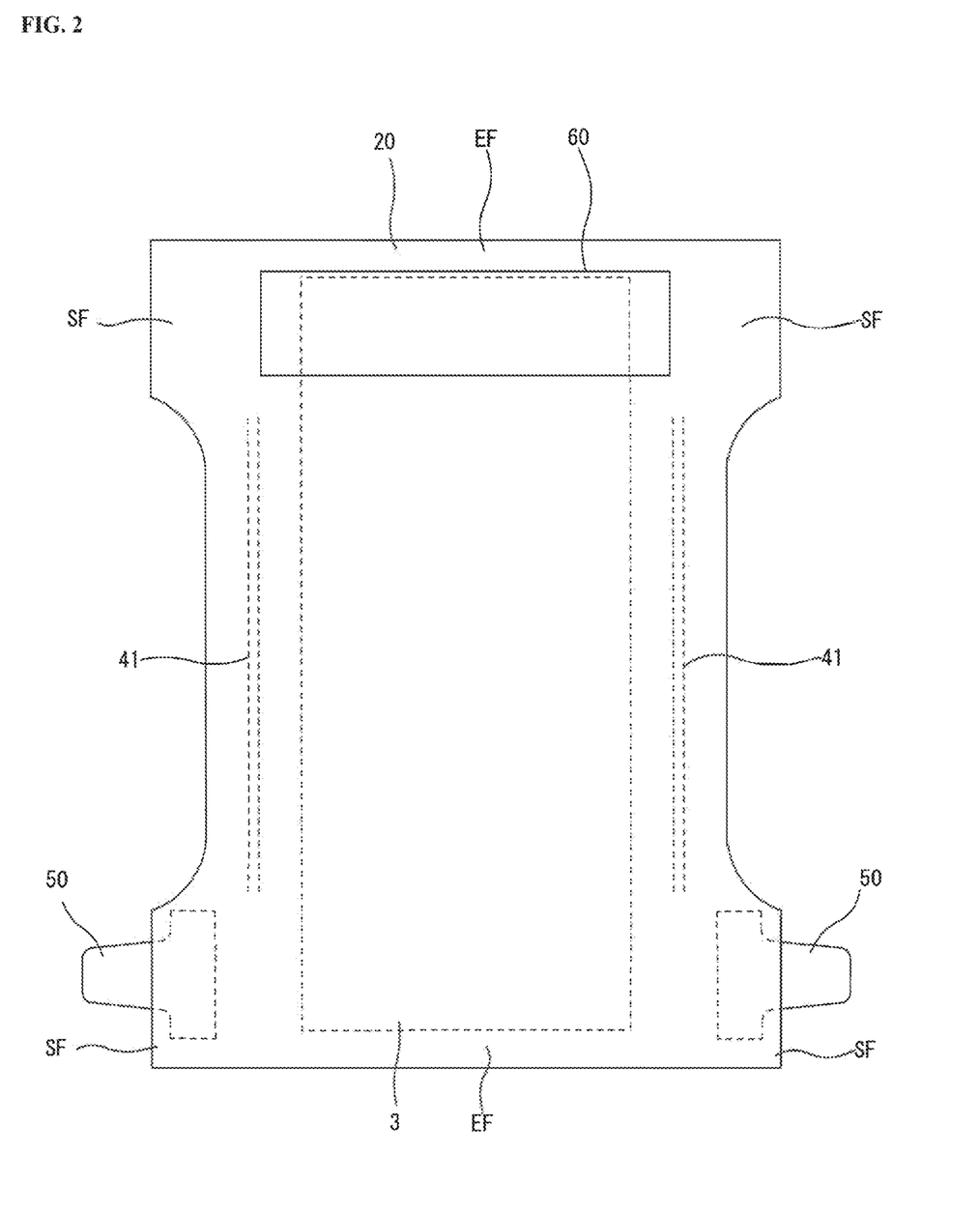
FIG. 2 is an exterior plan view of a disposable diaper in a developed state.

As shown in FIGS. 1 and 2, a disposable diaper 100 includes a liquid permeable top sheet 1 facing a wearer's body, a liquid impermeable back sheet 2 facing opposite to the wearer's body, and an absorbent pad 3 disposed between the top sheet 1 and the back sheet 2. An exterior sheet 20 is provided on an outer surface of the back sheet 2.

Three-dimensional gathers 30 are respectively formed on outer portions of the absorbent pad 3 in the width direction thereof, and flat gathers 40 are respectively formed on portions of the diaper outside the three-dimensional gathers 30. The three-dimensional gathers 30 and the flat gathers 40 respectively surround wearer's legs, and block excrement from leaking outside the diaper.

End flaps EF including no absorber body 3 are respectively present at portions of the diaper in front of and behind the absorbent pad 3 in the longitudinal direction thereof. Side flaps SF including no absorber body 3 are present respectively at portions of the diaper outside the absorber body 3 in the width direction thereof.

Fastening tapes 50 extending outward in the width direction are respectively provided for some of the side flaps SF on the back side, and a target sheet 60 for locking the fastening tapes 50 when the disposable diaper 100 is worn is provided on the belly side of an outer surface of the exterior sheet 20.

(Top Sheet)

The top sheet 1 has a portion extending outward from the outer periphery of the absorbent pad 3, and an outer surface of the extending portion is fixed to an inner surface of the back sheet 2 via an adhesive such as hot melt.

Examples of the top sheet 1 include a porous or non-porous nonwoven fabric, and a perforated plastic sheet. Examples of material fibers constituting the nonwoven fabric include olefin-, polyester-, and amide-based synthetic fibers such as polyethylene and polypropylene, regenerated fibers such as rayon and cupra, and natural fibers such as cotton. Examples of a method for processing the nonwoven fabric include known methods, such as spunlacing, spunbonding, SMS, thermobonding, meltblowing, needlepunching, air through bonding, and point bonding. In a preferred embodiment, the nonwoven fabric used as the top sheet 1 has a mass per unit area of 15 to 30 g/m², and a thickness of 0.05 to 1 mm (Back Sheet)

The back sheet 2 extends outward from an outer peripheral edge of the absorbent pad 3, and blocks the excrement absorbed by the absorbent pad 3 from moving to the outside.

The back sheet 2 may be, not only a plastic film such as a polyethylene film, but also a sheet having moisture permeability while keeping water impermeability in view of anti-humid properties. The water-impermeable and moisture-permeable sheet may be a microporous sheet obtained by melting and kneading an inorganic filler in an olefin-based resin such as polyethylene or polypropylene to form a sheet, and then stretching the sheet monoaxially or biaxially. In a preferred embodiment, the back sheet 2 has a weight per unit area of 13 g/m² to 40 g/m², and a thickness of 0.01 mm to 0.1 mm (Absorber)

Figure 5:
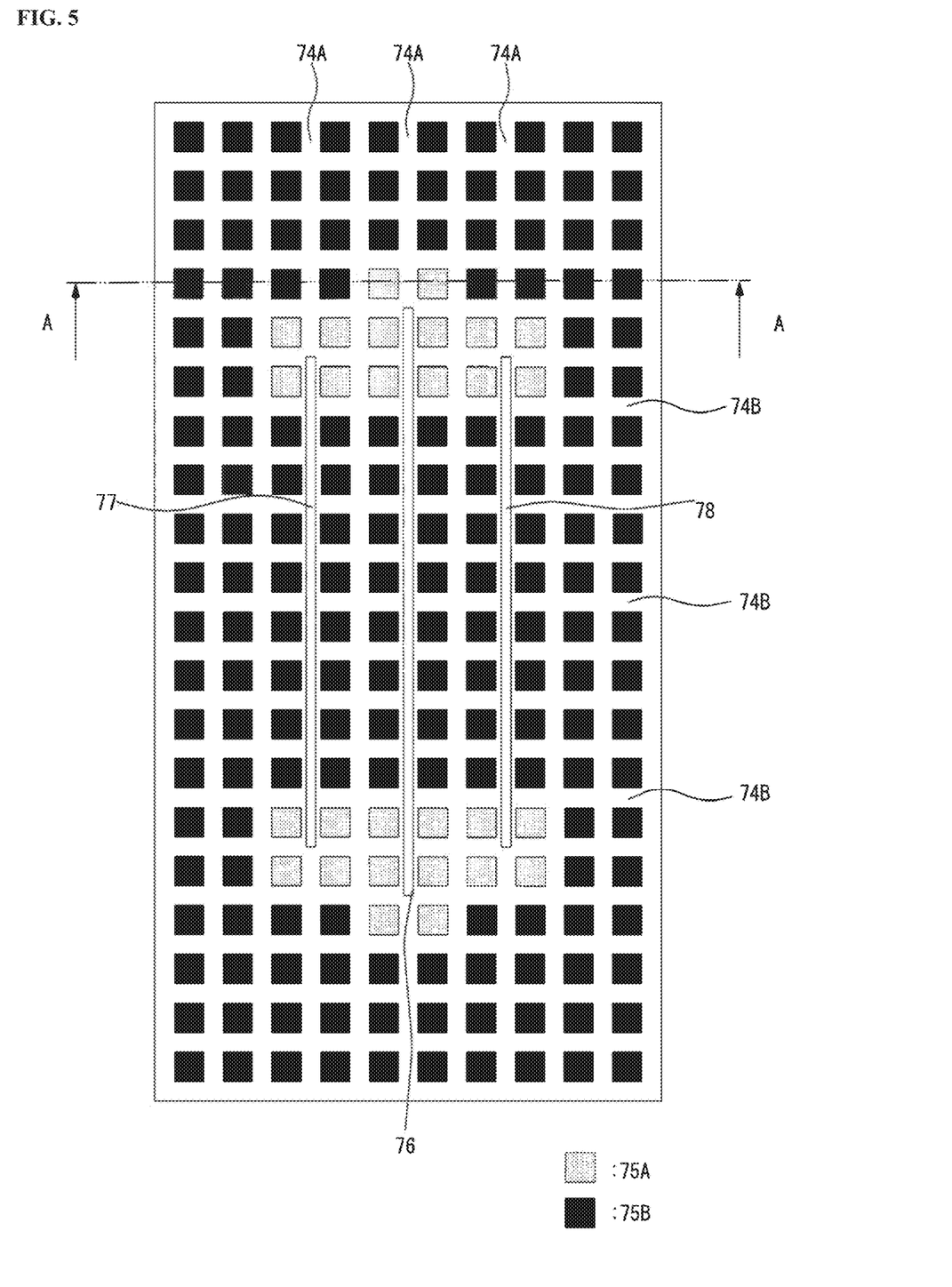
FIG. 5 is an interior plan view of an absorbent pad according to a first embodiment.
Figure 6:
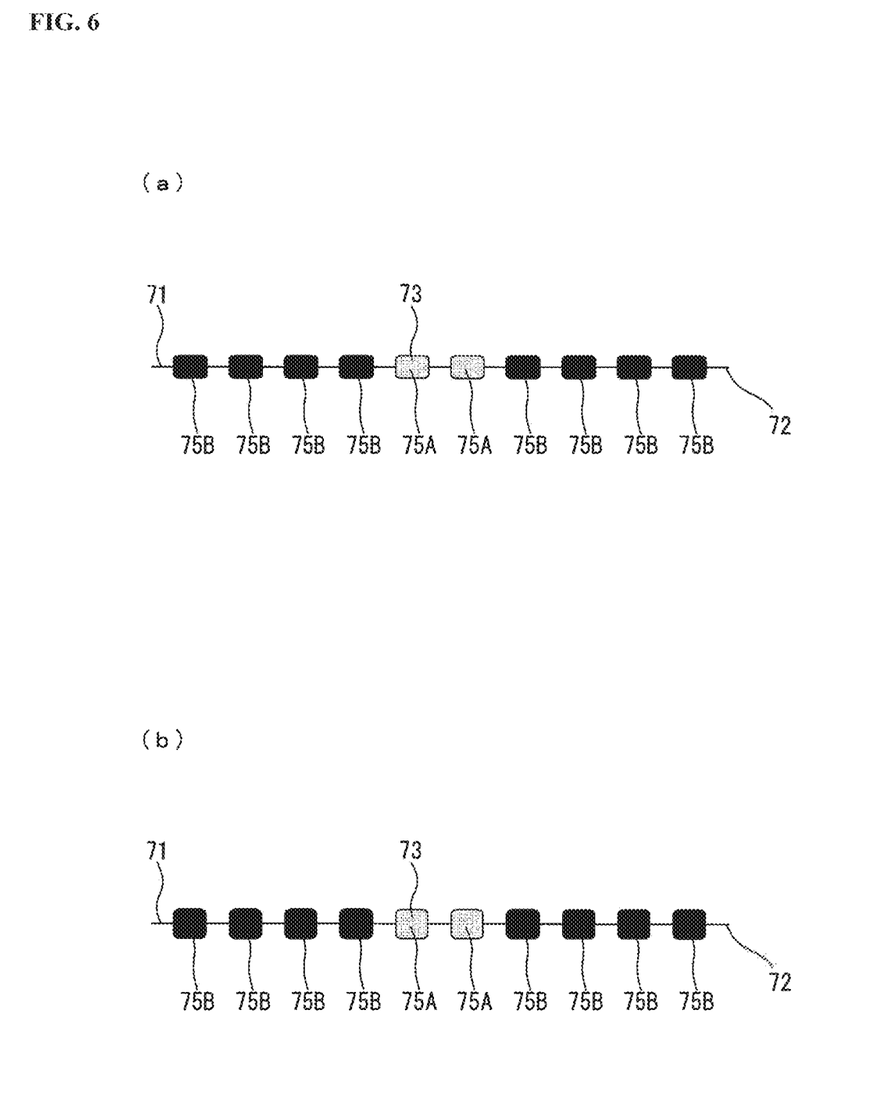

As shown in FIGS. 5, 6A, and 6B, the absorbent pad 3 of the first embodiment includes a liquid permeable front sheet 71 toward the top sheet 1, a liquid impermeable rear sheet 72 toward the back sheet 2, and absorbent polymer particles 73 disposed between the front and rear sheets 71 and 72.

The absorbent polymer particles 73 are contained in a plurality of cells 75 formed between the front and rear sheets 71 and 72. Each of the cells 75 is surrounded by junctions 74 where the front and rear sheets 71 and 72 are joined together. This can avoid the absorbent polymer particles 73 from concentrating on a portion of the absorbent pad 3, and can maintain the absorption performance of the absorbent pad 3. The absorbent polymer particles 73 may be unfixed to the front and rear sheets 71 and 72, or adhered to the front or rear sheet 71 or 72 via a hot melt adhesive. This can protect a blade of a cutter from chipping, enhancing productivity.

Among junctions 74A extending in the longitudinal direction, one in the middle of the absorbent pad 3 in the width direction ("first junction" recited in claims) is provided with an opening ("first opening" recited in claims) 76 elongated in the longitudinal direction. Thus, even when many cells 75 absorb the excretory fluid and swell to make the absorbent pad 3 more rigid, a portion of the absorbent pad 3 on the left of the opening 76 and a portion of the absorbent pad 3 on the right of the opening 76 easily move back and forth in response to the walk of the wearer, thereby reducing the sense of discomfort.

One of the junctions 74A extending in the longitudinal direction in a left portion of the absorbent pad 3 is provided with a left opening ("second opening" recited in claims) 77 elongated in the longitudinal direction. One of the junctions 74A extending in the longitudinal direction in a right portion of the absorbent pad 3 is provided with a right opening ("third junction" recited in claims) 78 elongated in the longitudinal direction. The left and right openings 77 and 78 are symmetric with respect to the opening 76. Thus, longitudinal movement of a portion of the absorbent pad 3 on the left of the left opening 77 in response to the walk of the wearer can be made greater than longitudinal movement of a portion of the absorbent pad 3 between the left opening 77 and the opening 76, thereby reducing the increase in the dimension of the opening 76 and the left opening 77 in the width direction. Likewise, longitudinal movement of a portion of the absorbent pad 3 on the right of the right opening 78 in response to the walk of the wearer can be made greater than longitudinal movement of a portion of the absorbent pad 3 between the right opening 78 and the opening 76, thereby reducing the increase in the dimension of the opening 76 and the right opening 78 in the width direction.

First cells 75A provided around front and rear ends of each of the opening 76, the left opening 77, and the right opening 78 in the longitudinal direction are filled with less absorbent polymer particles 73, and second cells 75A arranged in the other area are filled with more absorbent polymer particles 73. This enables easy deformation of portions of the absorbent pad around the front and rear ends of each of the opening 76, the left opening 77, and the right opening 78 in the longitudinal direction in response to the walk of the wearer, and can reduce the sense of discomfort.

Examples of the front sheet 71 include a porous or non-porous nonwoven fabric, and a perforated plastic sheet, as in the case of the top sheet 1. When the nonwoven fabric is selected, a nonwoven fabric having a high fiber density processed by spunbonding, meltblowing, or needlepunching is preferably used. When the plastic sheet is selected, a plastic sheet having pores of a smaller diameter than the outer diameter of the absorbent polymer particles 73 is preferably used. This can block the absorbent polymer particles 73 from falling off the cells 75.

Examples of the rear sheet 72 include a porous or non-porous nonwoven fabric, and a perforated plastic sheet, as in the case of the top sheet 1. When the nonwoven fabric is selected, a nonwoven fabric having a high fiber density processed by spunbonding, meltblowing, or needlepunching is preferably used. When the plastic sheet is selected, a plastic sheet having pores of a smaller diameter than the outer diameter of the absorbent polymer particles 73 is preferably used. This can block the absorbent polymer particles 73 from falling off the cells 75.

Examples of the absorbent polymer particles 73 include superabsorbent polymer particles used in absorbent articles such as disposable diapers and napkins. Examples of the superabsorbent polymer particles include starch-, cellulose-, and synthetic polymer-based particles, such as a starch-acrylic acid (salt) graft copolymer, a saponified product of a starch-acrylonitrile copolymer, a crosslinked product of sodium carboxymethyl cellulose, and an acrylic acid (salt) polymer.

In a preferred embodiment, the absorbent polymer particles 73 have a water absorption of 40 g/g or more, and a speed of water absorption of 70 seconds or less, in particular 40 seconds or less. This allows the absorbent pad 3 to efficiently absorb the excretion liquid which has passed through the top sheet 1, and can avoid what is called backflow of the excretory fluid across the top sheet 1.

In a preferred embodiment, the absorbent polymer particles 73 have a gel strength of 1000 Pa or more. This can make the absorbent pad 3 which has absorbed the excretory fluid less sticky.

In a preferred embodiment, the absorbent polymer particles 73 have a particle size determined such that, when the absorbent polymer particles 73 are sifted (shaked for five minutes) through a 500 μm standard sieve (JIS Z8801-1: 2006), and then the particles passed through the 500 μm standard sieve are sifted (shaked for five minutes) through a 180 μm standard sieve (JIS Z8801-1: 2006), the percentage of particles remaining on the 500 μm standard sieve is not more than 30% by weight, and the percentage of particles remaining on the 180 μm standard sieve is not less than 60% by weight.

In a preferred embodiment, the absorbent polymer particles 73 in the first cells 75A have a mass per unit area appropriately determined depending on the required absorption amount, e.g., 50 g/m² to 175 g/m². When the mass per unit area is less than 50 g/m², the absorption amount cannot be ensured. In a preferred embodiment, the absorbent polymer particles 73 in the second cells 75B have a mass per unit area appropriately determined depending on the required absorption amount, e.g., 175 g/m² to 350 g/m². When the mass per unit area exceeds 350 g/m², the absorption amount increases too much.

The dimension in the width direction of the junctions 74A extending in the longitudinal direction is 5 mm to 10 mm, and the dimension in the longitudinal direction of the junctions ("second junctions" recited in claims 74B extending in the width direction is 5 mm to 10 mm. The dimensions in the longitudinal direction and the width direction of each cell 75 are 10 mm to 150 mm. This allows the excretory fluid that has passed through the top sheet 1 to be diffused over the entire area of the absorbent pad 3, and allows the plurality of cells 75 to effectively absorb the excretory fluid.

In a preferred embodiment, the junctions 74 are formed through welding of the front and rear sheets 71 and 72 by, for example, ultrasonic welding or heat sealing. Alternatively, the junctions 74 may be formed through bonding with a hot melt adhesive. The cells 75, which are formed in a square shape when viewed in plan, may be in the shape of a rectangle, a rhombus, a hexagon, a circle, or an ellipse. If the cells 75 are hexagonal in shape, each of the junctions 74A extends in the longitudinal direction while zigzaging in the width direction along the shape in the width direction of the hexagonal shape. In a similar manner, the junctions 74B extends in the width direction while zigzaging in the longitudinal direction along the shape of the hexagonal shape in the longitudinal direction.

In a preferred embodiment, the opening 76 has a longitudinal dimension of 50% or more of a longitudinal dimension of the junction 74A extending in the longitudinal direction. A widthwise dimension of the opening 76 is not particularly limited. Note that the longitudinal dimension of the opening 76 of the first embodiment is approximately 62% of the longitudinal dimension of the junction 74A extending in the longitudinal direction, and the widthwise dimension of the opening 76 is approximately 50% of the widthwise dimension of the junction 74A extending in the longitudinal direction.

The longitudinal dimensions of the left opening 77 and the right opening 78 are not particularly limited, but are preferably less than 50% of the longitudinal dimension of the junction 74A extending in the longitudinal direction. Widthwise dimensions of the left opening 77 and the right opening 78 are not particularly limited. Note that the longitudinal dimensions of the left and right openings 77 and 78 of the first embodiment are about 47% of the longitudinal dimension of the junction 74A extending in the longitudinal direction, and the widthwise dimensions of the left and right openings 77 and 78 are about 50% of the widthwise dimension of the junction 74A extending in the longitudinal direction.

(Exterior Sheet)

The exterior sheet 20 covers the outer surface of the back sheet 2, and gives an outer surface of the disposable diaper 100 fabric-like appearance and texture. The exterior sheet 20 is preferably formed of a nonwoven fabric. Examples of material fibers include olefin-, polyester-, and polyamide-based synthetic fibers such as polyethylene and polypropylene, regenerated fibers such as rayon and cupra, and natural fibers such as cotton. The exterior sheet can be produced by spunlacing, spunbonding, thermobonding, air through bonding, and needlepunching, for example. In view of satisfactory texture and strength, long fiber nonwoven fabrics such as spunbonded nonwoven fabrics, SMS nonwoven fabrics, and SMMS nonwoven fabrics are preferably used.

A single sheet or a plurality of sheets of the nonwoven fabric may be used. When a plurality of sheets is used as a stack, the sheets are preferably fixed together with an adhesive such as a hot melt adhesive. When the nonwoven fabric is used, the nonwoven fabric preferably has a mass per unit area of 10 g/m² to 50 g/m², in particular 15 g/m² to 30 g/m².

(Leg-Surrounding Three-Dimensional Gather)

Figure 3:
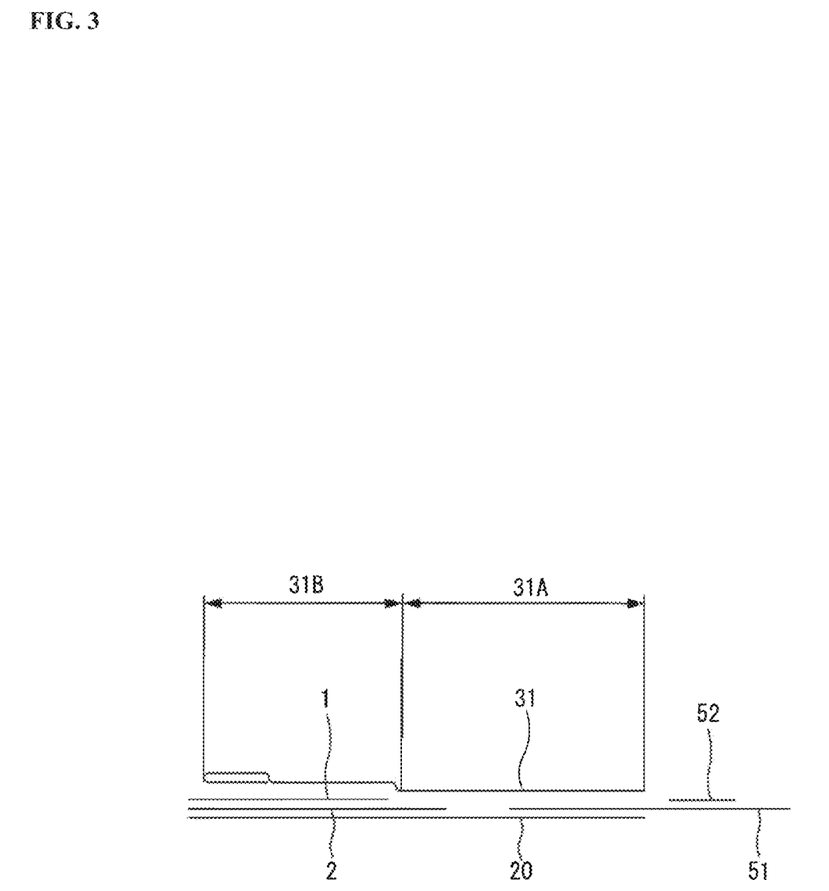
FIG. 3 is a cross-sectional view taken along line A-A in FIG. 1.
Figure 4:
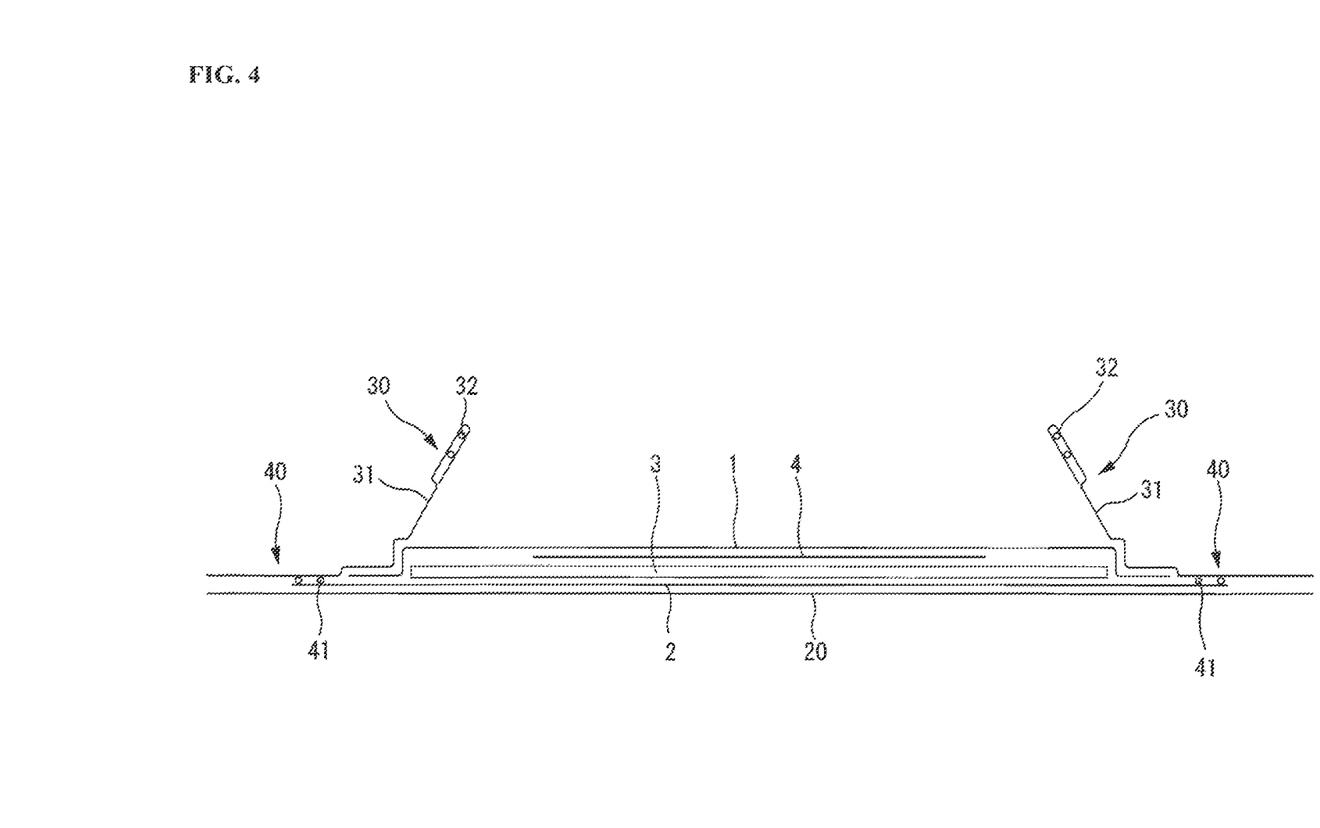
FIG. 4 is a cross-a sectional view taken along line B-B in FIG. 1.

As shown in FIGS. 3 and 4, gather sheets 31 respectively forming the three-dimensional gathers 30 surrounding the legs each have a base 31A, an outer surface of which is fixed to the back sheet 2 and the exterior sheet 20 across the longitudinal direction, in particular, to an outer portion in the width direction of the inner surface of the back sheet 2 and an outer portion in the width direction of the inner surface of the exterior sheet 20. Each of the gather sheets 31 also has an erectable portion 31B, front and rear end portions of which in the longitudinal direction are respectively fixed to outer portions in the width direction of the inner surface of the top sheet 1. A middle portion in the longitudinal direction of each of the erectable portions 31B of the gather sheets 31 is not fixed to, but is spaced apart from, the inner surface of the top sheet 1.

Each of the erectable portions 31B of the gather sheets 31 is provided with two or more elongated elastic stretchable strips 32 arranged at predetermined intervals in the width direction. The elastic stretchable strips 32 extend in the longitudinal direction, and are stretched to a predetermined degree. Thus, when the disposable diaper 100 is worn, the erectable portions 31B are erected toward a crotch portion of the wearer by the action of a contractive force of the elastic stretchable strips 32. This can press distal ends of the erectable portions 31B against the wearer's crotch portion to block the excrement from leaking to the outside.

Examples of the gather sheet 31 include, in addition to a nonwoven fabric such as a spunbonded nonwoven fabric, a plastic film similar to that used for the back sheet 2, and a stack of these sheets. However, in view of texture felt by skin, a nonwoven fabric given with water repellency is preferably used.

The elastic stretchable strips 32 may be made of natural or synthetic rubber formed in the shape of a thread, a string, or a belt. In particular, a material generally used in the art, such as styrene-based rubber, olefin-based rubber, urethane-based rubber, ester-based rubber, polyurethane, polyethylene, polystyrene, styrene butadiene, silicone, and polyester can be used. In a preferred embodiment, the elastic stretchable strips 32 have a thickness of about 500 dtex to 1500 dtex, in particular about 800 dtex to 1300 dtex (about 0.1 mm to 3 mm, in particular about 0.5 mm to 3 mm when natural rubber is used), and an extension ratio of about 150% to 250%, in particular about 160% to 200% in an attached state.

(Leg-Surrounding Flat Gather)

The flat gathers 40 surrounding the legs are provided on the bases 31A of the gather sheets 31 forming the three-dimensional gathers 30. Two or more elastic stretchable strips 41 are arranged at predetermined intervals in the width direction on outer portions in the width direction of the bases 31A of the gather sheets 31 and an outer portion of the back sheet 2, the outer portions forming the side flaps SF. The elastic stretchable strips 32 extend in the longitudinal direction, and are stretched to a predetermined degree. Thus, when the disposable diaper 100 is worn, the flat gathers 40 are pressed onto the legs of the wearer by the action of a contractive force of the elastic stretchable strips 41. This can block the excrement from leaking to the outside.

The elastic stretchable strips 41 may be made of natural or synthetic rubber formed in the shape of a thread, a string, or a belt. In particular, a material generally used in the art, such as styrene-based rubber, olefin-based rubber, urethane-based rubber, ester-based rubber, polyurethane, polyethylene, polystyrene, styrene butadiene, silicone, and polyester can be used. The interval between the elastic stretchable strips 41 is preferably about 2 mm to 15 mm, more preferably about 3 mm to 7 mm. In a preferred embodiment, the elastic stretchable strips 41 have a thickness of about 500 dtex to 1500 dtex, in particular about 800 dtex to 1300 dtex (about 0.1 mm to 3 mm, in particular about 0.5 mm to 3 mm when natural rubber is used), and an extension ratio of about 150% to 250%, in particular about 160% to 200% in an attached state.

(Fastening Tape)

As shown in FIGS. 1 to 3, fastening tapes 50 extending outward are provided on the back side portion of the side flap portion SF. Each of the fastening tapes 50 includes a base sheet 51, and a locking portion 52 provided on an outer portion of an inner surface of the base sheet 51. An inner portion of the base sheet 51 is fixed to the outer portion of the gather sheet 31 and the outer portion of the exterior sheet 20 in the width direction.

The base sheet 51 is preferably made of a nonwoven fabric, and any known nonwoven fabric can be used without particular limitation. Examples of fibers constituting the nonwoven fabric include olefin-, polyester-, and amide-based synthetic fibers such as polyethylene and polypropylene, regenerated fibers such as rayon and cupra, and natural fibers such as cotton. Examples of a method for producing the nonwoven fabric include known methods, such as spunlacing, spunbonding, SMS, thermobonding, meltblowing, needlepunching, air through bonding, and point bonding. A spunbonded nonwoven fabric and an SMS nonwoven fabric using olefin fibers are particularly preferred. The nonwoven fabric to be used can have a basis weight determined as appropriate. However, in a preferred embodiment, a main body 5b has a total basis weight of the nonwoven fabric of 20 g/m$^2$ to 75 g/m$^2$, in particular 26 g/m$^2$ to 46 g/m$^2$, and a fixing portion 5f and a distal end portion 5p have a total basis weight of the nonwoven fabric of 35 g/m$^2$ to 130 g/m$^2$, in particular 46 g/m$^2$ to 116 g/m$^2$. Within the ranges, a base portion of the fastening tape fixed between the exterior sheet 20 and the gather sheet 31 can ensure strength and rigidity, and the main body 74 can ensure flexibility and stretchability.

In a preferred embodiment, the locking portion 52 is a hook member of a mechanical fastener. The hook member has multiple engaging projections. The engaging projections may have any shape, such as: (A) a mirror-inverted J shape; (B) J shape; (C) a mushroom shape; (D) T shape; and (E) a dual J shape (a combination of two Js joined together back to back like a fishhook). Alternatively, an adhesive layer may replace the hook member.

(Target Sheet)

In a preferred embodiment, the target sheet 60 is made of a plastic film or a nonwoven fabric having multiple loops formed on a surface thereof. This allows the locking portions 52 of the fastening tapes 50 to be efficiently locked onto the target sheet 60 when the wearer puts the disposable diaper 100 on.

(Intermediate Sheet)

In the first embodiment, an intermediate sheet 4 is provided between the top sheet 1 and the absorbent pad 3. Thus, the excretory fluid that has passed through the top sheet 1 can be quickly moved to the absorbent pad 3 to block the backflow of the excretory fluid. The intermediate sheet 4 is fixed to the outer surface of the top sheet 1 with a hot melt adhesive, or through heat embossing or ultrasonic welding.

Examples of the intermediate sheet 4 include, in addition to a nonwoven fabric, a resin film having multiple permeable pores. Examples of the nonwoven fabric include those usable as the top sheet 1, but in a preferred embodiment, a nonwoven fabric higher in hydrophilicity or fiber density than the top sheet 1 is used because it can efficiently move the excretory fluid from the top sheet 1 to the intermediate sheet 4.

<Absorbent Pad of Second Embodiment>

An absorbent pad 3 according to a second embodiment will be described below. The same reference numerals are given to the same components as those of the absorbent pad 93 of the first embodiment, and a description thereof will not be repeated.

Figure 7:
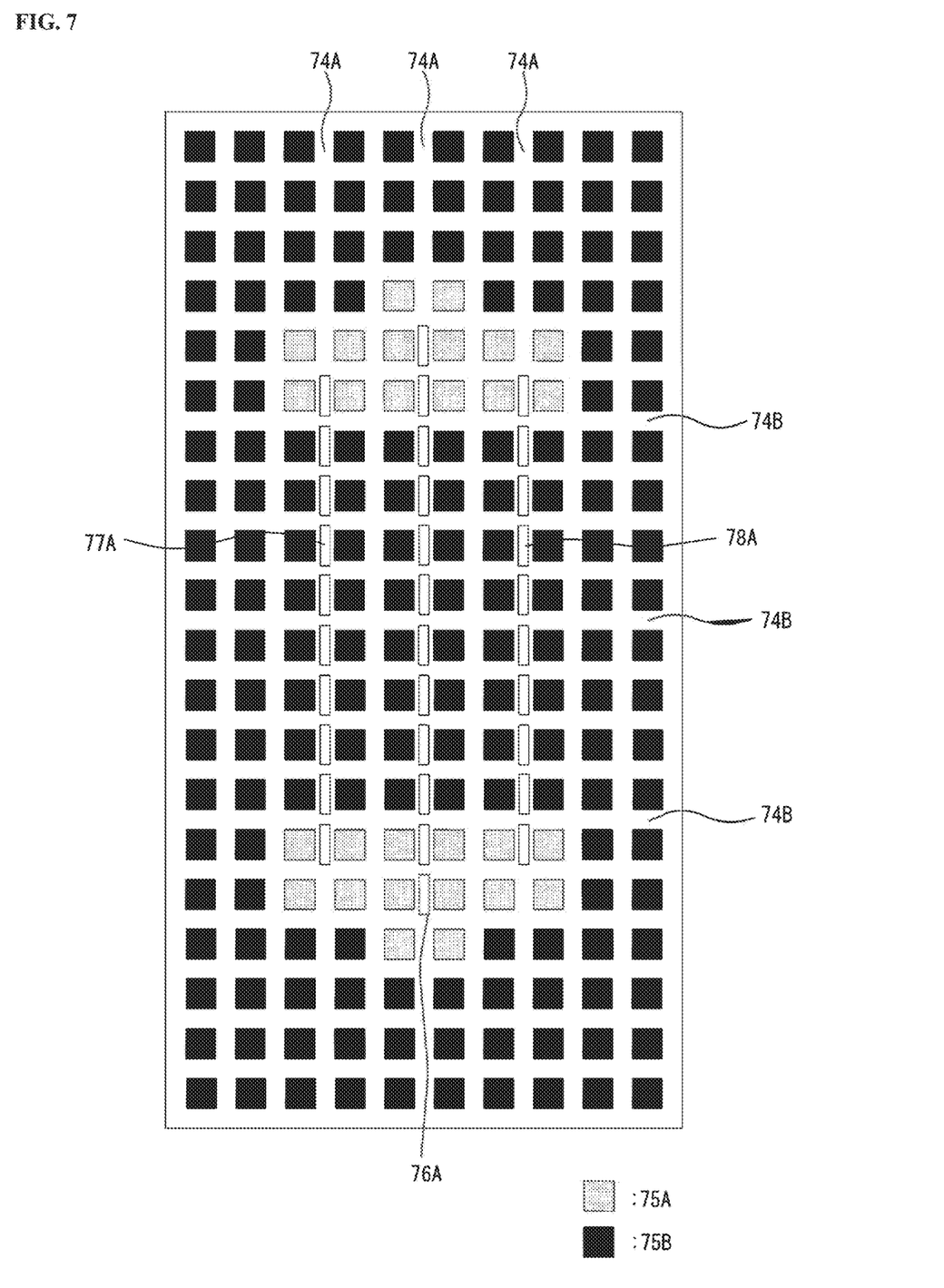
FIG. 7 is an interior plan view of an absorbent pad according to a second embodiment.

As shown in FIG. 7, the junction 74A extending in the longitudinal direction in the middle of the absorbent pad 3 in the width direction is provided with a set of openings 76A which are arranged at predetermined intervals in the longitudinal direction and elongated in the longitudinal direction. Each of the openings 76A is formed in a rectangular shape having long sides parallel to the longitudinal direction. Thus, even when many cells 75 absorb the excretory fluid and swell to make the absorbent pad 3 more rigid, a portion of the absorbent pad 3 on the left of the openings 76A and a portion of the absorbent pad 3 on the right of the openings 76A easily move back and forth in response to the walk of the wearer, thereby reducing the sense of discomfort, and protecting the cells 75 arranged near the openings 76A from break.

One of the junctions 74A extending in the longitudinal direction in a left portion of the absorbent pad 3 is provided with a set of left openings 77A which are arranged at predetermined intervals in the longitudinal direction and elongated in the longitudinal direction. One of the junctions 74A extending in the longitudinal direction in a right portion of the absorbent pad 3 is provided with a set of right openings 78A which are arranged at predetermined intervals in the longitudinal direction and elongated in the longitudinal direction. Each of the left and right openings 77A and 78A is formed in a rectangular shape having long sides parallel to the longitudinal direction. Thus, longitudinal movement of a portion of the absorbent pad 3 on the left of left openings 77A in response to the walk of the wearer can be made greater than longitudinal movement of a portion of the absorbent pad 3 between the left openings 77A and the openings 76A, thereby reducing the increase in the dimensions of the openings 76A and the left openings 77A in the width direction, and protecting the cells 75 arranged near the left openings 77A from break. Likewise, longitudinal movement of a portion of the absorbent pad 3 on the right of the right openings 78A in response to the walk of the wearer can be made greater than longitudinal movement of a portion of the absorbent pad 3 between the right openings 78A and the openings 76A, thereby reducing the increase in the dimensions of the openings 76A and the right openings 78A in the width direction, and protecting the cells 75 arranged near the right openings 78A from break.

The set of openings 76A may have a longitudinal dimension of 50% or more of a longitudinal dimension of the junction 74A extending in the longitudinal direction. The interval between the openings 76A in the longitudinal direction and a widthwise dimension of each of the openings 76A are not particularly limited. Note that the longitudinal dimension of the set of openings 76A of the second embodiment is approximately 62% of the length of the junction 74A extending in the longitudinal direction. The interval between the openings 76A in the longitudinal direction and the widthwise dimension of each of the openings 76A are approximately 50% of the widthwise dimension of the junction 74A extending in the longitudinal direction.

The longitudinal dimension of the set of left openings 77A and the longitudinal dimension of the set of right openings 78A are not particular limited, but preferably less than 50% of the length of the junction 74A extending in the longitudinal direction. The intervals between the left openings 77A, the intervals between the right openings 78A, and the widthwise dimensions of the left and right openings are not particularly limited. Note that in the second embodiment, the longitudinal dimension of the set of left openings 77A and the longitudinal dimension of the set of right openings 78A are approximately 47% of the length of the junction 74A extending in the longitudinal direction. The interval between the left openings 77A, the interval between the right openings 78A, and the widthwise dimension of each of the left and right openings 77 and 78 are approximately 50% of the widthwise dimension of the junction 74A extending in the longitudinal direction.

<Absorbent Pad of Third Embodiment>

The absorbent pad 3 according to the third embodiment will be described below. The same reference numerals are given to the same components as those of the absorbent pad 93 of the first embodiment, and a description thereof will not be repeated.

Figure 8:
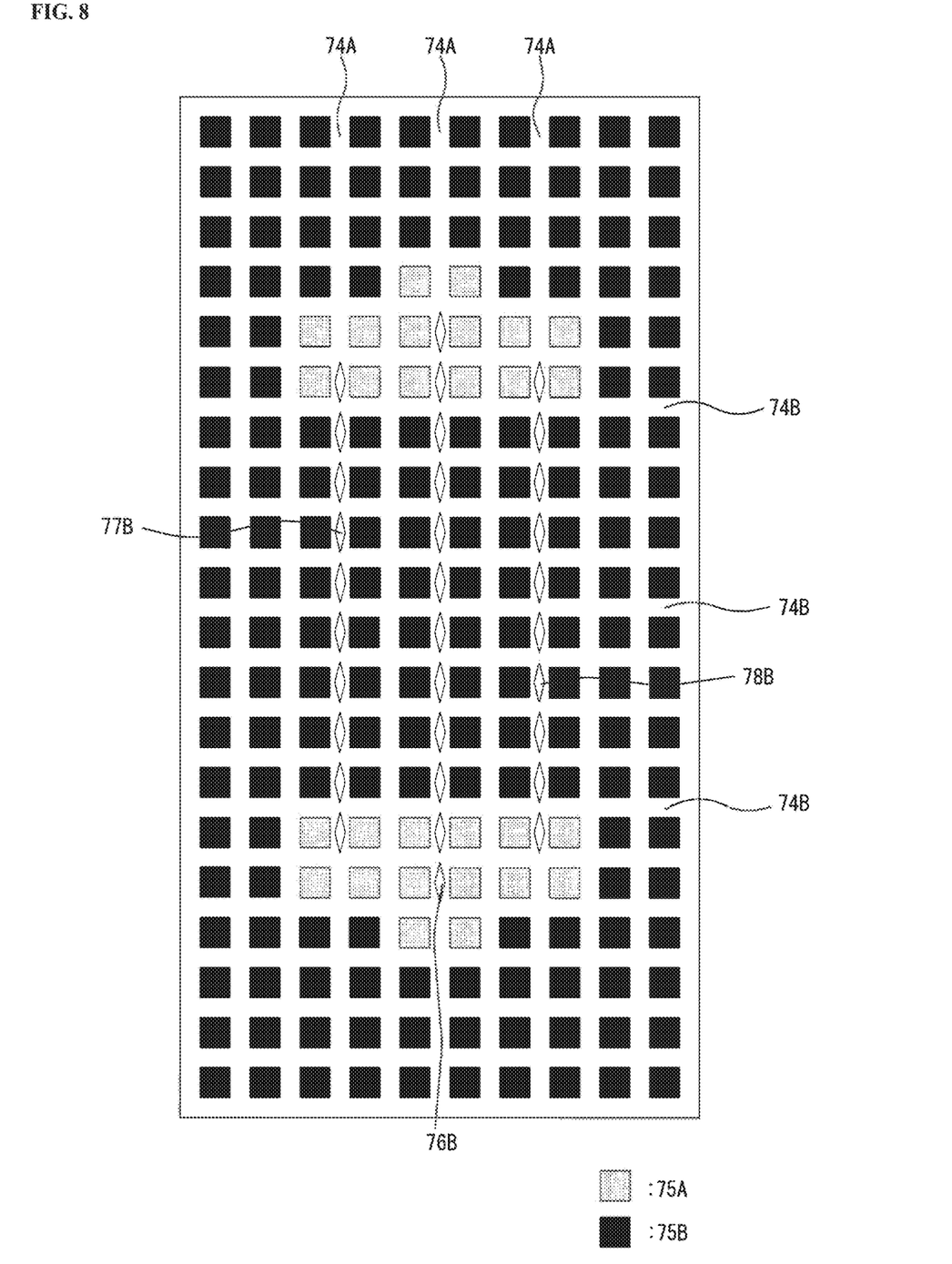
FIG. 8 is an interior plan view of an absorbent pad according to a third embodiment.

As shown in FIG. 8, the junction 74A extending in the longitudinal direction in the middle of the absorbent pad 3 in the width direction is provided with a set of openings 76B which are arranged at predetermined intervals in the longitudinal direction and elongated in the longitudinal direction. Each of the openings 76B is formed in a rhombic shape whose long diagonal line is parallel to the longitudinal direction. Thus, even when many cells 75 absorb the excretory fluid and swell to make the absorbent pad 3 more rigid, a portion of the absorbent pad 3 on the left of the openings 76B and a portion of the absorbent pad 3 on the right of the openings 76B easily move back and forth in response to the walk of the wearer, thereby reducing the sense of discomfort, and further protecting the cells 75 arranged near the openings 76B from break.

One of the junctions 74A extending in the longitudinal direction in a left portion of the absorbent pad 3 in the width direction is provided with a set of left openings 77B which are arranged at predetermined intervals in the longitudinal direction and elongated in the longitudinal direction. One of the junctions 74A extending in the longitudinal direction in a right portion of the absorbent pad 3 is provided with a set of right openings 78B which are arranged at predetermined intervals in the longitudinal direction and elongated in the longitudinal direction. Each of the left and right openings 77B and 78B is formed in a rhombic shape whose long diagonal line is parallel to the longitudinal direction. Thus, longitudinal movement of a portion of the absorbent pad 3 on the left of left openings 77B in response to the walk of the wearer can be made greater than longitudinal movement of a portion of the absorbent pad 3 between the left openings 77B and the openings 76B, thereby reducing the increase in the dimensions of the openings 76B and the left openings 77B in the width direction, and further protecting the cells 75 arranged near the left openings 77B from break. Likewise, longitudinal movement of a portion of the absorbent pad 3 on the right of the right openings 78B in response to the walk of the wearer can be made greater than longitudinal movement of a portion of the absorbent pad 3 between the right openings 78B and the openings 76B, thereby reducing the increase in the dimensions of the openings 76B and the right openings 78B in the width direction, and further protecting the cells 75 arranged near the right openings 78B from break.

The set of openings 76B may have a longitudinal dimension of 50% or more of a longitudinal dimension of the junction 74A extending in the longitudinal direction. The interval between the openings 76B in the longitudinal direction and a widthwise dimension of each of the openings 76B are not particularly limited. Note that the longitudinal dimension of the set of openings 76B of the third embodiment is approximately 62% of the length of the junction 74A extending in the longitudinal direction. The interval between the openings 76B in the longitudinal direction and the widthwise dimension of each of the openings 76B are approximately 50% of the widthwise dimension of the junction 74A extending in the longitudinal direction.

The longitudinal dimensions of the set of left openings 77B and the set of right openings 78B are not particularly limited, but are preferably less than 50% of the longitudinal dimension of the junction 74A extending in the longitudinal direction. The interval between the left openings 77B, the interval between the right openings 78B, and a widthwise dimension of each of the left and right openings 77B and 78B are not particularly limited. Note that in the third embodiment, the longitudinal dimension of the set of left openings 77B and the longitudinal dimension of the set of right openings 78B are approximately 47% of the length of the junction 74A extending in the longitudinal direction. The interval between the left openings 77B, the interval between the right openings 78B, and the widthwise dimension of each of the left and right openings 77B and 78B are approximately 50% of the widthwise dimension of the junction 74A extending in the longitudinal direction.

<Absorbent Pad of Fourth Embodiment>

An absorbent pad 3 according to the fourth embodiment will be described below. The same reference numerals are given to the same components as those of the absorbent pad 93 of the first embodiment, and a description thereof will not be repeated.

Figure 9:
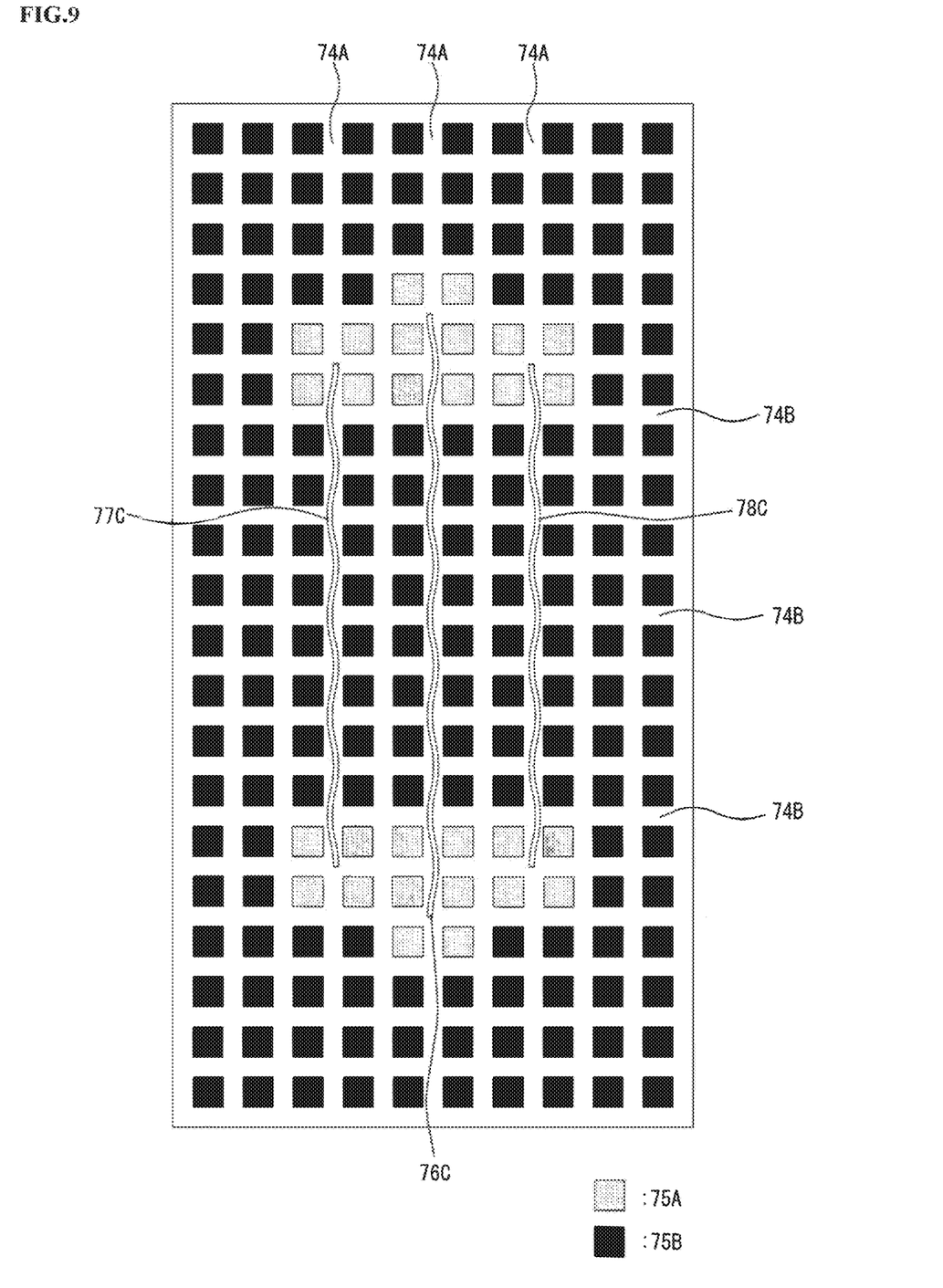
FIG. 9 is an interior plan view of an absorbent pad according to a fourth embodiment.

As shown in FIG. 9, the junction 74A extending in the longitudinal direction in the middle of the absorbent pad 3 in the width direction is provided with an opening 76C extending in a waveform in the longitudinal direction. Thus, even when many cells 75 absorb the excretory fluid and swell to make the absorbent pad 3 more rigid, a portion of the absorbent pad 3 on the left of the opening 76C and a portion of the absorbent pad 3 on the right of the opening 76C easily move back and forth in response to the walk of the wearer, thereby further reducing the sense of discomfort.

One of the junctions 74A extending in the longitudinal direction in a left portion of the absorbent pad 3 is provided with a left opening 77C extending in a waveform in the longitudinal direction. One of the junctions 74A extending in the longitudinal direction in a right portion of the absorbent pad 3 is provided with a right opening 78C extending in a waveform in the longitudinal direction. Thus, longitudinal movement of a portion of the absorbent pad 3 on the left of the left opening 77C in response to the walk of the wearer can be made greater than longitudinal movement of a portion of the absorbent pad 3 between the left opening 77C and the opening 76C, thereby further reducing the increase in the dimension of the opening 76C and the left opening 77C in the width direction. Likewise, longitudinal movement of a portion of the absorbent pad 3 on the right of the right opening 78C in response to the walk of the wearer can be made greater than longitudinal movement of a portion of the absorbent pad 3 between the right opening 78C and the opening 76C, thereby further reducing the increase in the dimension of the opening 76C and the right opening 78C in the width direction.

The opening 76C may have a longitudinal dimension of 50% or more of a longitudinal dimension of the junction 74A extending in the longitudinal direction. A whole dimension of the opening 76C measured from its left end to right end of the waveform, and a dimension of the opening 76C in the width direction are not particularly limited. Note that the longitudinal dimension of the opening 76C of the fourth embodiment is approximately 62% of the longitudinal dimension of the junction 74A extending in the longitudinal direction, the whole dimension of the opening 76C is approximately 90% of the widthwise dimension of the junction 74A extending in the longitudinal direction, and the widthwise dimension of the opening 76C is approximately 50% of the widthwise dimension of the junction 74A extending in the longitudinal direction.

The longitudinal dimensions of the left opening 77C and the right opening 78C are not particularly limited, but are preferably less than 50% of the longitudinal dimension of the junction 74A extending in the longitudinal direction. The whole dimension of the left opening 77C measured from its left end to right end of the waveform, the whole dimension of the right opening 78C measured from its left end to right end of the waveform, and a widthwise dimension of each of the left and right openings 77C and 78C are not particularly limited. Note that the longitudinal dimensions of the left and right openings 77C and 78C of the fourth embodiment are approximately 47% of the longitudinal dimension of the junction 74A extending in the longitudinal direction, the whole dimensions of the left and right openings 77B and 78B are approximately 90% of the widthwise dimension of the junction 74A extending in the longitudinal direction, and the widthwise dimensions of the left and right openings 77B and 78B are about 50% of the widthwise dimension of the junction 74A extending in the longitudinal direction.

<Absorbent Pad of Fifth Embodiment>

An absorbent pad 3 according to the fifth embodiment will be described below. The same reference numerals are given to the same components as those of the absorbent pad 93 of the first embodiment, and a description thereof will not be repeated.

Figure 10:
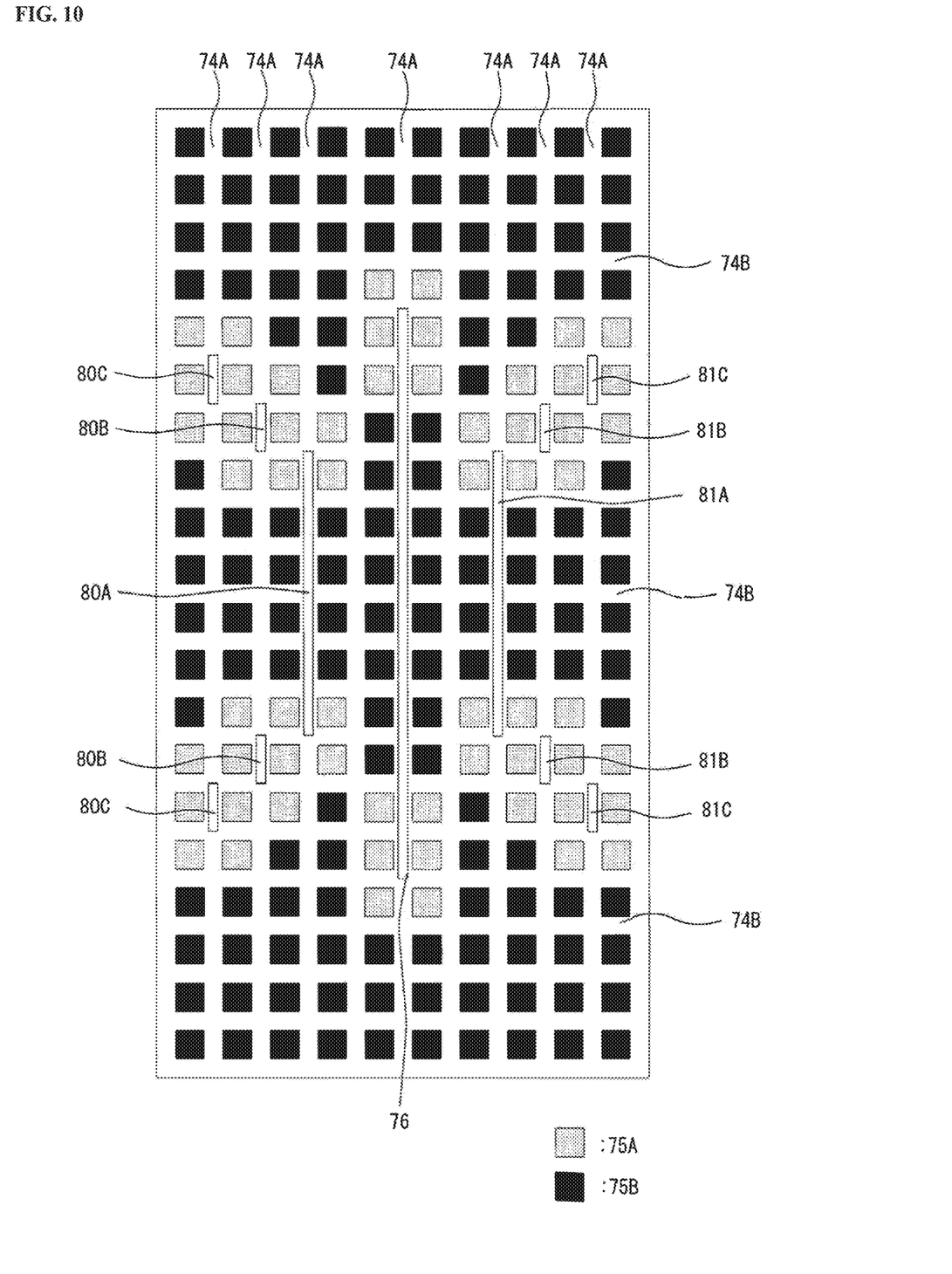
FIG. 10 is an interior plan view of an absorbent pad according to a fifth embodiment.

As shown in FIG. 10, one of the junctions 74A extending in the longitudinal direction in a left portion of the absorbent pad 3 is provided with a first left opening 80A extending in the longitudinal direction. Two other junctions 74A on the left of the former junction 74A extending in the longitudinal direction are respectively provided with second left openings 80B and third left openings 80C, each of which extends in the longitudinal direction.

When viewed in plan, a virtual line connecting the longitudinal center of the first left opening 80A, the longitudinal midpoint between the front and rear second left openings 80B, and the longitudinal midpoint between the front and rear third left openings 80C is preferably in an arc shape.

In a preferred embodiment, when viewed from the left (when the absorbent pad 3 in FIG. 10 is viewed from the left to the right), which is a direction perpendicular to the direction seeing the plan view of the absorbent pad 3, the front third left opening 80C has a rear end located at a front end of the front second left opening 80B. The front second left opening 80B has a rear end located at a front end of the first left opening 80A. The first left opening 80A has a rear end located at a front end of the rear second left opening 80B. The rear second left opening 80B has a rear end located at a front end of the rear third left opening 80C. Thus, when the absorbent pad 3 is viewed from the left, the first left opening 80A, the second left openings 80B, and the third left openings 80C are substantially arranged in a straight line.

Thus, a portion of the absorbent pad 3 on the left of the third left openings 80C, a portion of the absorbent pad 3 between the third left openings 80C and the second left openings 80B, a portion of the absorbent pad 3 between the second left openings 80B and the first left opening 80A, and a portion of the absorbent pad 3 between the first left opening 80A and the opening 76 are allowed to make longitudinal movements in response to the walk of the wearer in such a manner that the further leftward portion makes the greater longitudinal movement. This can further reduce the increase in the widthwise dimensions of the opening 76C, the first left opening 80A, the second left openings 80B, and the third left openings 80C.

One of the junctions 74A extending in the longitudinal direction in a right portion of the absorbent pad 3 is provided with a first right opening 81A extending in the longitudinal direction. Two other junctions 74A on the right of the former junction 74A extending in the longitudinal direction are respectively provided with second right openings 81B and third right openings 81C, each of which extends in the longitudinal direction. Note that a set of the first right opening 81A, the second right openings 81B, and the third right openings 81C and a set of the first left opening 80A, the second left openings 80B, and the third left openings 80C are symmetric with respect to the opening 76.

When viewed in plan, a virtual line connecting the longitudinal center of the first right opening 81A, the longitudinal midpoint between the front and rear second right openings 81B, and the longitudinal midpoint between the front and rear third right openings 81C is preferably in an arc shape.

In a preferred embodiment, when viewed from the left, which is a direction perpendicular to the direction seeing the plan view of the absorbent pad 3, the front third right opening 81C has a rear end located at a front end of the front second right opening 81B. The front second right opening 81B has a rear end located at a front end of the first right opening 81A. The first right opening 81A has a rear end located at a front end of the rear second right opening 81B. The rear second right opening 81B has a rear end located at a front end of the rear third right opening 81C. Thus, when the absorbent pad 3 is viewed from the right, the first right opening 81A, the second right openings 81B, and the third right openings 81C are substantially arranged in a straight line.

Thus, a portion of the absorbent pad 3 on the right of the third right openings 81C, a portion of the absorbent pad 3 between the third right openings 81C and the second right openings 81B, a portion of the absorbent pad 3 between the second right openings 81B and the first right opening 81A, and a portion of the absorbent pad 3 between the first right opening 81A and the opening 76 are allowed to make longitudinal movements in response to the walk of the wearer in such a manner that the further rightward portion makes the greater longitudinal movement. This can further reduce the increase in the widthwise dimensions of the opening 76, the first right opening 81A, the second right openings 81B, and the third right openings 81C.

The sum of the longitudinal dimensions of the first left opening 80A, the second left openings 80B, and the third left openings 80C is not particularly limited, but is preferably less than 50% of the length of the junction 74A extending in the longitudinal direction. Widthwise dimensions of the first left opening 80A, the second left openings 80B, and the third left openings 80C are not particularly limited. Likewise, the sum of the longitudinal dimensions of the first right opening 81A, the second right openings 81B, and the third right openings 81C is not particularly limited, but is preferably less than 50% of the length of the junction 74A extending in the longitudinal direction. Widthwise dimensions of the first right opening 81A, the second right openings 81B, and the third right openings 81C are not particularly limited. Note that the sum of the longitudinal dimensions of the first left opening 80A, the second left openings 80B, and the third left openings 80C of the fifth embodiment is approximately 47% of the length of the junction 74A extending in the longitudinal direction, and the widthwise dimension of each of the first left opening 80A, the second left openings 80B, and the third left openings 80C is approximately 50% of the widthwise dimension of the junction 74A extending in the longitudinal direction. Further, the sum of the longitudinal dimensions of the first right opening 81A, the second right openings 81B, and the second right openings 81C is approximately 47% of the length of the junction A extending in the longitudinal direction, and the widthwise dimension of each of the first right opening 81A, the second right openings 81B, and the third right openings 81C is approximately 50% of the widthwise dimension of the junction 74A extending in the longitudinal direction.

The present invention is applicable to absorbent articles, such as disposable diapers with tapes, pant-shaped disposable diapers, napkins, and pads.

The invention claimed is:

1. An absorbent pad comprising:
   a liquid permeable front sheet, a liquid permeable or impermeable rear sheet, and absorbent polymer particles disposed between the front sheet and the rear sheet, the absorbent polymer particles absorbing excretory fluid,
   wherein the front sheet and the rear sheet are joined to each other at a plurality of first junctions and a plurality of second junctions,
   when viewed in plan, the first junctions each extending in a longitudinal direction are arranged at predetermined intervals in a width direction, and the second junctions each extending in the width direction are arranged at predetermined intervals in the longitudinal direction,
   a plurality of cells, each of which is defined by an adjacent pair of the first junctions and an adjacent pair of the second junctions, is formed between the front sheet and the rear sheet spaced apart from each other,
   the absorbent polymer particles are provided in the cells, and
   an opening extending in the longitudinal direction is formed in at least one of the first junctions;
   wherein the cells include first cells containing the absorbent polymer particles in a small amount and second cells containing the absorbent polymer particles in a large amount, and the first cells are arranged around both ends in the longitudinal direction of the opening.

2. The absorbent pad of claim 1, wherein the opening includes a first opening provided at one of the first junctions at a center of the absorbent pad in the width direction, a second opening provided at one of the first junctions in a left portion of the absorbent pad in the width direction, and a third opening provided at one of the first junctions in a right portion of the absorbent pad in the width direction.

3. The absorbent pad of claim 2, wherein a dimension of the first opening in the longitudinal direction is greater than dimensions of the second and third openings in the longitudinal direction.

4. The absorbent pad of claim 2, wherein each of the first, second, and third openings is formed of discontinuous breaking openings.

5. The absorbent pad of claim 4, wherein when viewed in plan, the second opening is formed in an arc shape toward the center in the width direction, and the third opening is formed in an arc shape toward the center in the width direction.

6. The absorbent pad of claim 3, wherein each of the first, second, and third openings is formed of discontinuous breaking openings.

* * * * *